(12) United States Patent
Hogan et al.

(10) Patent No.: US 9,868,795 B2
(45) Date of Patent: *Jan. 16, 2018

(54) VINYL MODIFIER COMPOSITION AND PROCESSES FOR UTILIZING SUCH COMPOSITION

(71) Applicant: Bridgestone Corporation, Chuo-ku (JP)

(72) Inventors: Terrence E. Hogan, Uniontown, OH (US); Waruna C. B. Kiridena, Copley, OH (US)

(73) Assignee: Bridgestone Corporation, Chuo-ku (JP)

( * ) Notice: Subject to any disclaimer, the term of this patent is extended or adjusted under 35 U.S.C. 154(b) by 14 days.

This patent is subject to a terminal disclaimer.

(21) Appl. No.: 15/080,108

(22) Filed: Mar. 24, 2016

(65) Prior Publication Data

US 2016/0237181 A1 Aug. 18, 2016

Related U.S. Application Data

(63) Continuation of application No. 14/682,594, filed on Apr. 9, 2015, now Pat. No. 9,309,330, which is a
(Continued)

(51) Int. Cl.
*C08F 2/38* (2006.01)
*C08F 36/04* (2006.01)
(Continued)

(52) U.S. Cl.
CPC ............. *C08F 2/38* (2013.01); *B60C 1/00* (2013.01); *C07D 307/12* (2013.01); *C08F 36/04* (2013.01); *C07B 2200/09* (2013.01)

(58) Field of Classification Search
CPC .. C08F 4/48; C08F 36/00; C08F 36/04; C08F 36/06; C08F 36/10; C08F 236/00; C08F 236/04; C08F 236/06; C08F 236/10
See application file for complete search history.

(56) References Cited

U.S. PATENT DOCUMENTS 3,207,742 A 9/1965 Castle et al.
3,451,988 A 6/1969 Langer, Jr. et al.
(Continued)

FOREIGN PATENT DOCUMENTS

EP 0215256 A1 3/1987
EP 0355597 A1 2/1990
(Continued)

OTHER PUBLICATIONS

Pennakem (Sales Specifications: 2,2-Di(tetrahydrofuryl)propane. PennaKem. Jul. 15, 2003, 1 page).*
(Continued)

*Primary Examiner* — Brieann R Johnston
(74) *Attorney, Agent, or Firm* — Meredith E. Hooker; Jenny L. Sheaffer

(57) ABSTRACT

An oxolanyl compound-containing composition comprising specified amounts of the meso-isomer of one or more of the oxolanyl compounds of specified structure is provided. Also provided are methods for the use of such compositions as vinyl content modifiers in polymerization processes.

26 Claims, 6 Drawing Sheets

Effect of Concentration of DTHFP (and Meso Content) on 1,2-Vinyl Content of Polybutadiene.

Related U.S. Application Data continuation of application No. 13/518,711, filed as application No. PCT/US2010/061795 on Dec. 22, 2010, now Pat. No. 9,062,017.

(60) Provisional application No. 61/288,900, filed on Dec. 22, 2009.

(51) Int. Cl.

| C08F 36/06 | (2006.01) |
|---|---|
| C08F 236/04 | (2006.01) |
| C08F 236/06 | (2006.01) |
| C08F 236/10 | (2006.01) |
| C07D 307/12 | (2006.01) |
| B60C 1/00 | (2006.01) |

(56) References Cited

U.S. PATENT DOCUMENTS

| 4,022,959 A | 5/1977 | Sommer et al. |
|---|---|---|
| 4,247,418 A | 1/1981 | Halasa et al. |
| 4,280,927 A | 7/1981 | Lohr, Jr. |
| 4,401,800 A | 8/1983 | Hall |
| 4,429,090 A | 1/1984 | Hall |
| 4,429,091 A | 1/1984 | Hall |
| 4,537,939 A | 8/1985 | Hall et al. |
| 4,577,035 A | 3/1986 | Huffman et al. |
| 4,591,624 A | 5/1986 | Hall |
| 4,647,635 A | 3/1987 | Hall |
| 4,696,986 A | 9/1987 | Halasa et al. |
| 5,112,929 A | 5/1992 | Hall |
| 5,210,145 A | 5/1993 | Lawson et al. |
| 5,231,153 A | 7/1993 | Hsu et al. |
| 5,268,439 A | 12/1993 | Hergenrother et al. |
| 5,334,665 A | 8/1994 | Lawson et al. |
| 5,359,016 A | 10/1994 | Hsu et al. |
| 5,393,721 A | 2/1995 | Kitamura et al. |
| 5,448,003 A | 9/1995 | Hsu et al. |
| 5,550,200 A | 8/1996 | Shibata et al. |
| 6,071,847 A | 6/2000 | Cole et al. |
| 6,262,204 B1 | 7/2001 | Muller et al. |
| 6,384,150 B2 | 5/2002 | Hergenrother et al. |
| 6,579,997 B1 | 6/2003 | Gray et al. |
| 6,693,160 B1 | 2/2004 | Halasa et al. |
| 7,087,549 B2 | 8/2006 | Halasa et al. |
| 7,179,864 B2 | 2/2007 | Wang |
| 7,279,527 B2 | 10/2007 | Harwood et al. |
| 9,062,017 B2 | 6/2015 | Hogan et al. |
| 9,309,330 B2 | 4/2016 | Hogan et al. |
| 2006/0030671 A1 | 2/2006 | Boerner et al. |
| 2006/0241265 A1 | 10/2006 | Harwood et al. |
| 2008/0015309 A1 | 1/2008 | Ozawa et al. |

FOREIGN PATENT DOCUMENTS

| EP | 0507222 A1 | 10/1992 |
|---|---|---|
| EP | 0622381 A1 | 11/1994 |
| GB | 781721 A | 8/1957 |
| JP | S62-227906 A | 10/1987 |
| JP | H05-255425 A | 10/1993 |
| JP | H06-239909 A | 8/1994 |
| JP | 2003-155398 A | 5/2003 |
| JP | 2005-248107 A | 9/2005 |
| WO | 9210497 A1 | 6/1992 |
| WO | 2008100309 A1 | 8/2008 |

OTHER PUBLICATIONS

Universal Selector (Ditetrahydrofurylpropane (DTHFP)-Penn A Kem-datasheet. 2015, 2 pages).*
Office action from Japanese application No. 2014-160488 (dated Jan. 19, 2016).
Office action from Korean application No. 10-2012-7019142 (dated Jan. 6, 2017).
Lucht, Brett L., et al., "Polydentate Amine and Ether Solvates of Lithium Hexamethyldisilazide (LiHMDS): Relationship of Ligand Structure, Relative Solvation Energy, and Aggregation State," J. Am. Chem. Soc., vol. 118, pp. 10707-10718, 1996.
Hogan, Terrence L., et al., "The Effect of Stereochemistry in Anionic Polymerization Modifiers," Presented at the Fall 190th Technical Meeting of the Rubber Division, American Chemical Society, Oct. 11-13, 2016.
Hay, B. P. et al., "Search for Improved Host Architectures: Application of de Novo Structure-Based Design and High-Throughput Screening Methods to Identify Optimal Building Blocks for Multidentate Ethers," Journal of the American Chemical Society, vol. 127, pp. 17043-17053 (Feb. 11, 2005).
Ege, Seyhan, Organic Chemistry Second Edition, Chapter 6: Stereochemistry, pp. 180-222 (1989).
Langer, Jr., A.W., "New Chelated Organolithium Polymerization Catalysts," Polymer Reprints, American Chemical Society Division of Polymer Chemistry, vol. 7, No. 1, pp. 132-139 (Jan. 1966).
Micovic, V. M. et al., "The reaction of lead tetra-acetate with some unbranched alpha, omega-dials," Tetrahedron, Elsevier Science Publishers, vol. 25, pp. 985-993 (Jan. 1, 1969).
Monahan, Jennifer et al., "Cross-Linking the Protein Precursor of Marine Mussel Adhesives: Bulk Measurements and Reagents for Curing," Langmuir, vol. 20, pp. 3724-3729 (2004).
Paul, Raymond et al, "Structure de quelques produits de la condensation du sylvanne avec le dihydropyranne en presence d'anhydride sulfureux," Bulletin de la Societe Chimique de France, Societe Francaise de Chimie, pp. 2139-2144 (Jan. 1, 1961).
Sever, Mary J. et al., "Metal-Mediated Cross-Linking in the Generation of a Marine-Mussel Adhesive," Angewandte Chemie Int'l Ed., vol. 43, pp. 447-450 (2004).
Sotoca Usina, E., International Search Report with Written Opinion from PCT/US2010/061795, 18 pp. (dated Mar. 25, 2011).
Wang, Xiaorong et al., "Viscoelastic behavior of fullerene end-capped linear polymers," Polymer, vol. 47, Issue 18, pp. 6267-6271 (2006).
Westwood, Glenn et al., "Simplified Polymer Mimics of Cross-Linking Adhesive Proteins," Macromolecules, vol. 40, Issue 11, pp. 3960-3964 (2007).
Chinese Patent Office, English translation of Notification to Make Divisional Application from Chinese Application No. 201080064552.9, 3 pp. (dated Feb. 7, 2014).
Chinese Patent Office, English translation of Notification to Make Divisional Application from Chinese Application No. 201080064552.9, 2 pp. (dated Jun. 5, 2014).
Chinese Patent Office, Office Action with English translation from Chinese Application No. 201080064552.9, 11 pp. (dated Dec. 3, 2014).
Sotoca Usina, E., Office Action from European Application No. 10803323.4, 5 pp. (dated Apr. 18, 2013).
Response to European Office Action from European Application No. 10803323.4, 14 pp. (dated Jul. 31, 2013).
European Patent Office, EPO Rule 71(3) Intent to Grant from European Application No. 10803323.4, 7 pp. (dated Nov. 7, 2014).
European Patent Office, Decision to Grant from European Application No. 10803323.4, 1 pg. (dated Mar. 27, 2014).
Okazaki, T., Office Action with English translation from Japanese Application No. 2012-546196, 11 pp. (dated Apr. 15, 2014).
Japan Patent Office, Notice of Grant from Japanese Application No. 2012-546196, 3 pp. (dated Jul. 8, 2014).
Russian Patent Office, Office Action with English translation from Russian Application No. 2012131116, 8 pp. (dated Dec. 11, 2014).
Declaration of Terrence E. Hogan, pp. 1-11 (Jan. 26, 2015).
Declaration of Waruna Kiridena, 8 pp. (Jan. 23, 2015).
Yagimoto, K., Office Action with English translation from Japanese Application No. 2014-160488, 6 pp. (dated Aug. 18, 2015).
Office action from Korean application No. 10-2012-7019142 (dated Jul. 2017).

* cited by examiner

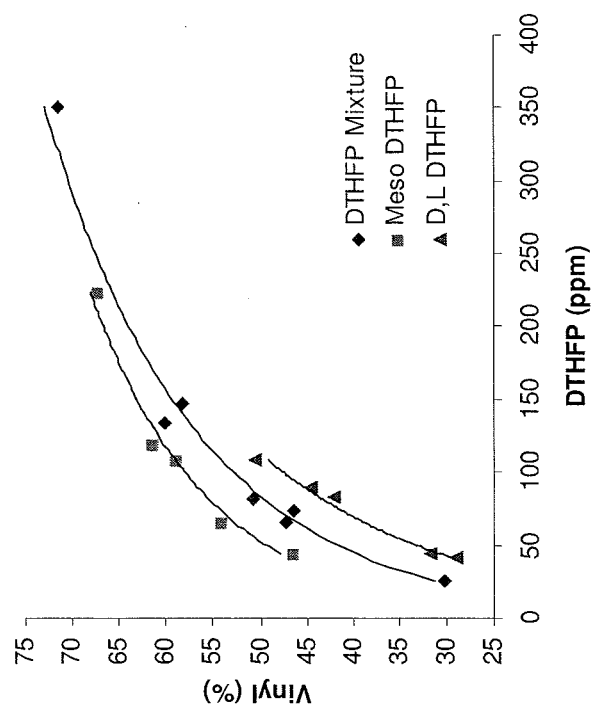
FIGURE 1: Effect of Concentration of DTHFP (and Meso Content) on 1,2-Vinyl Content of Polybutadiene.

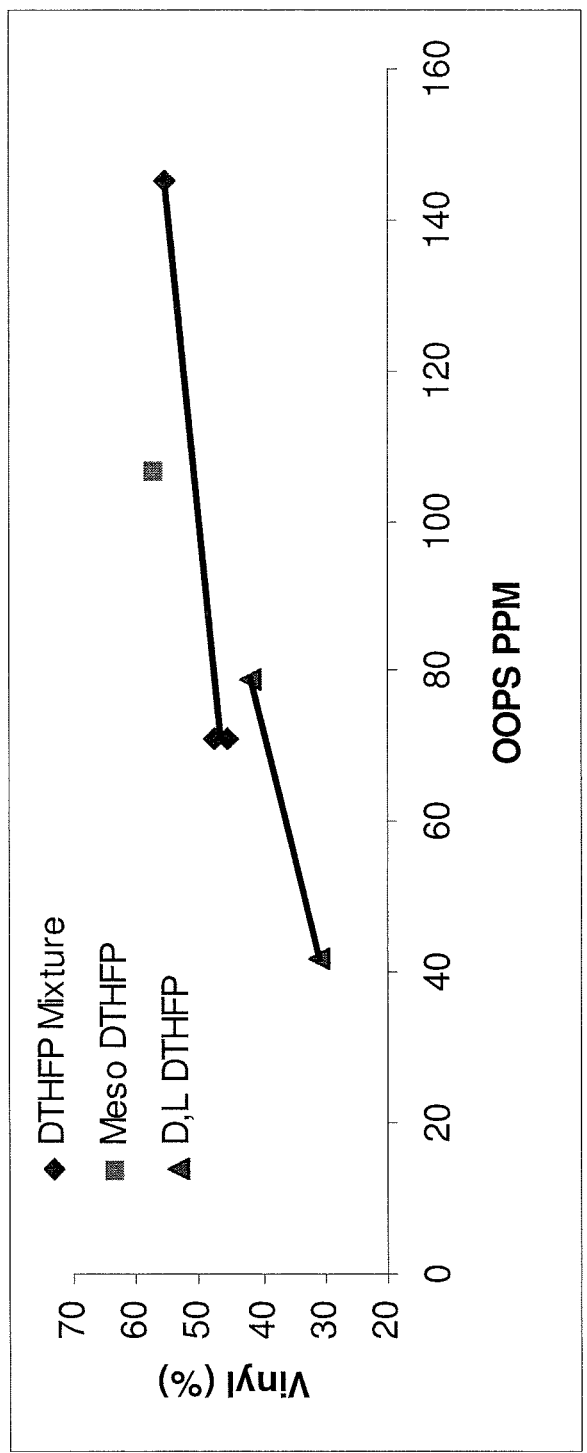
FIGURE 2: Effect of Concentration of DTHFP (and Meso Content) on 1,2-Vinyl Content of Styrene-Butadiene Copolymer.

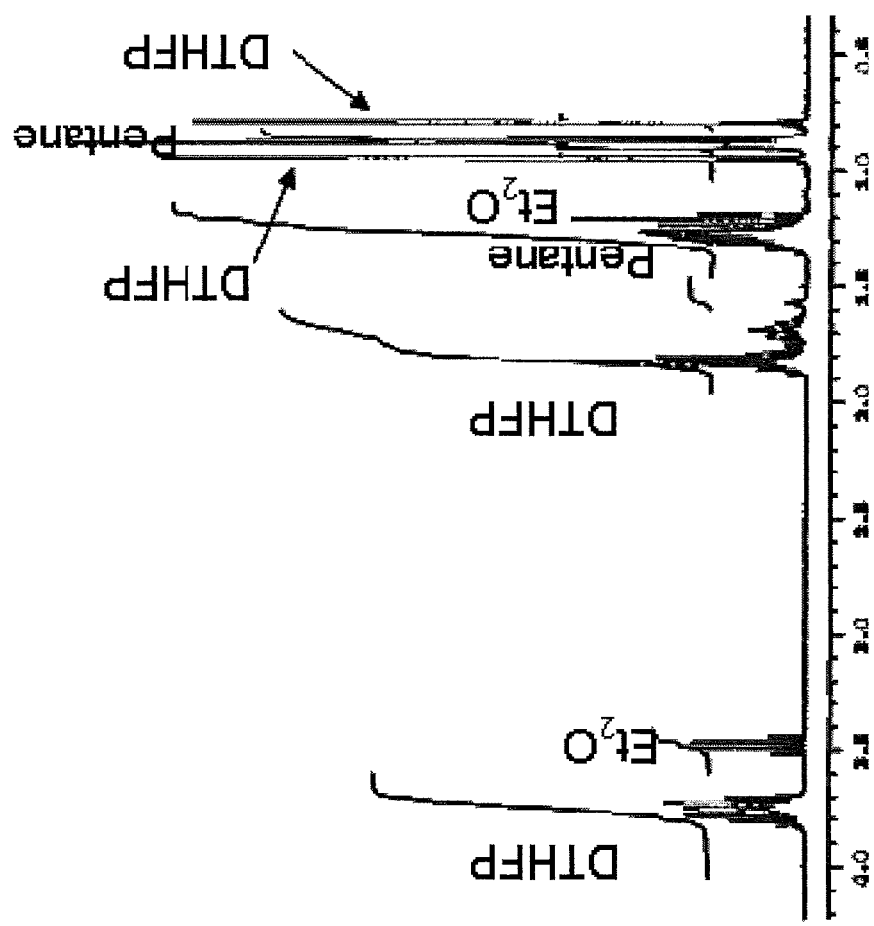
FIGURE 3: $^1$H NMR of meso-2,2-ditetrahydrofurylpropane.

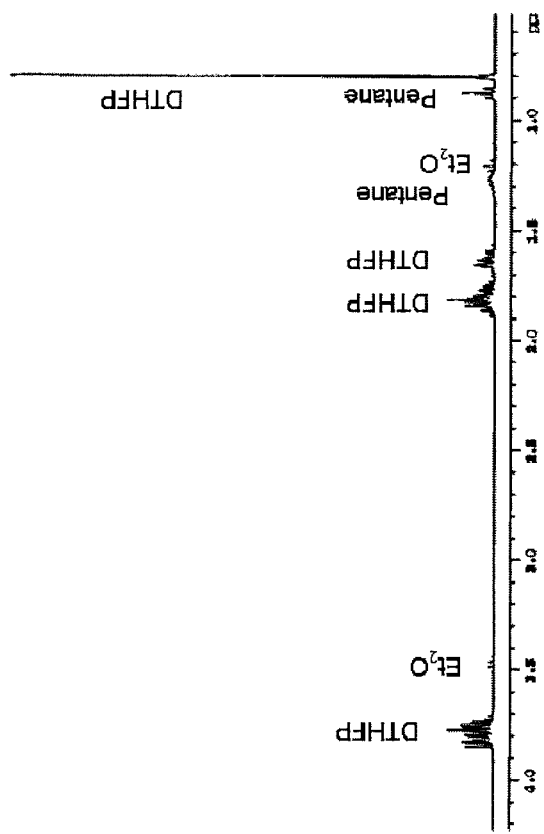
FIGURE 4: $^1$H NMR of D,L-2,2-ditetrahydrofurylpropane.

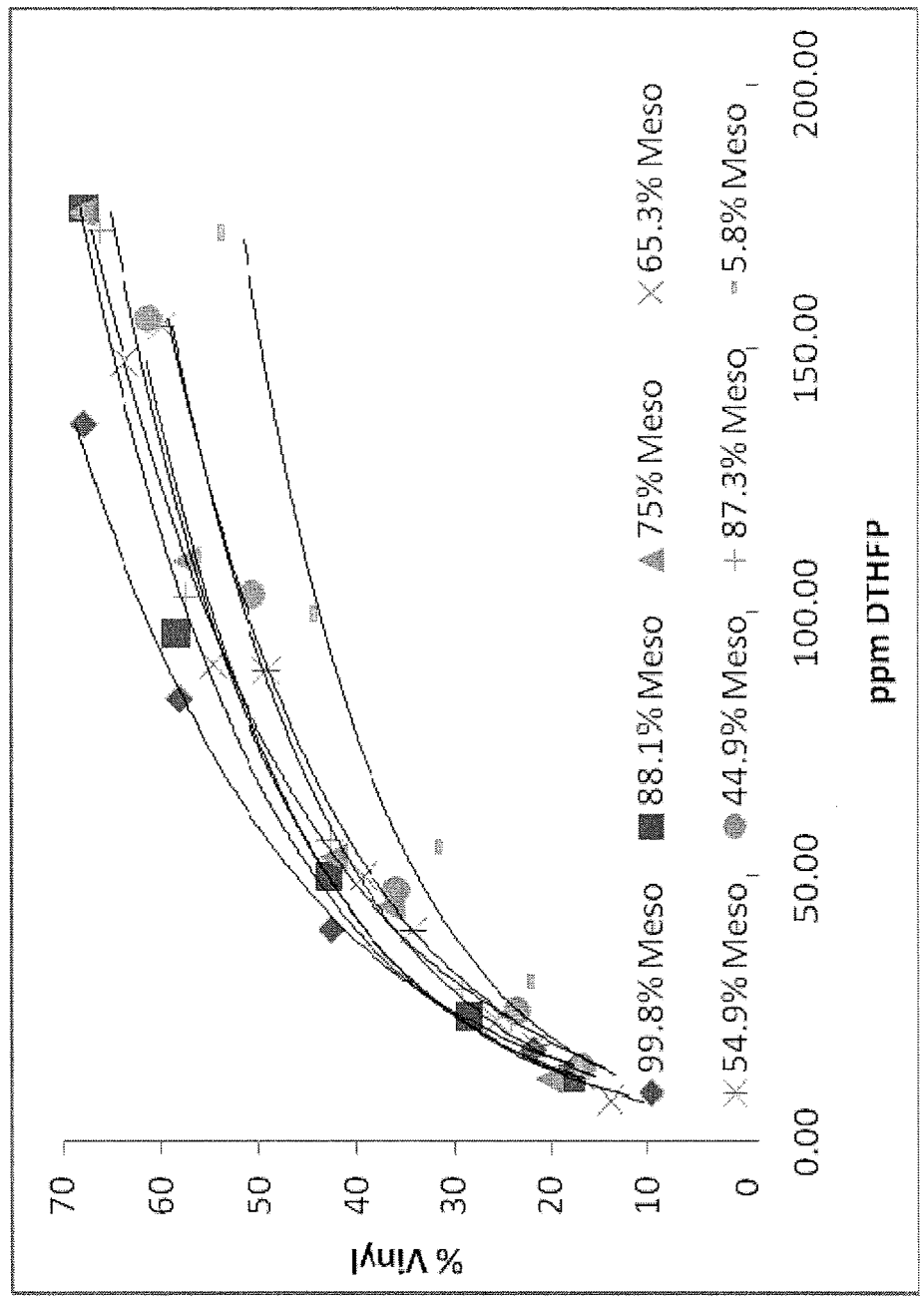
FIGURE 5: Effect of Meso Content of 2,2-ditetrahydrofurylpropane (at constant 2,2-ditetrahydrofurylpropane concentration) on 1,2-Vinyl Content of Polybutadiene.

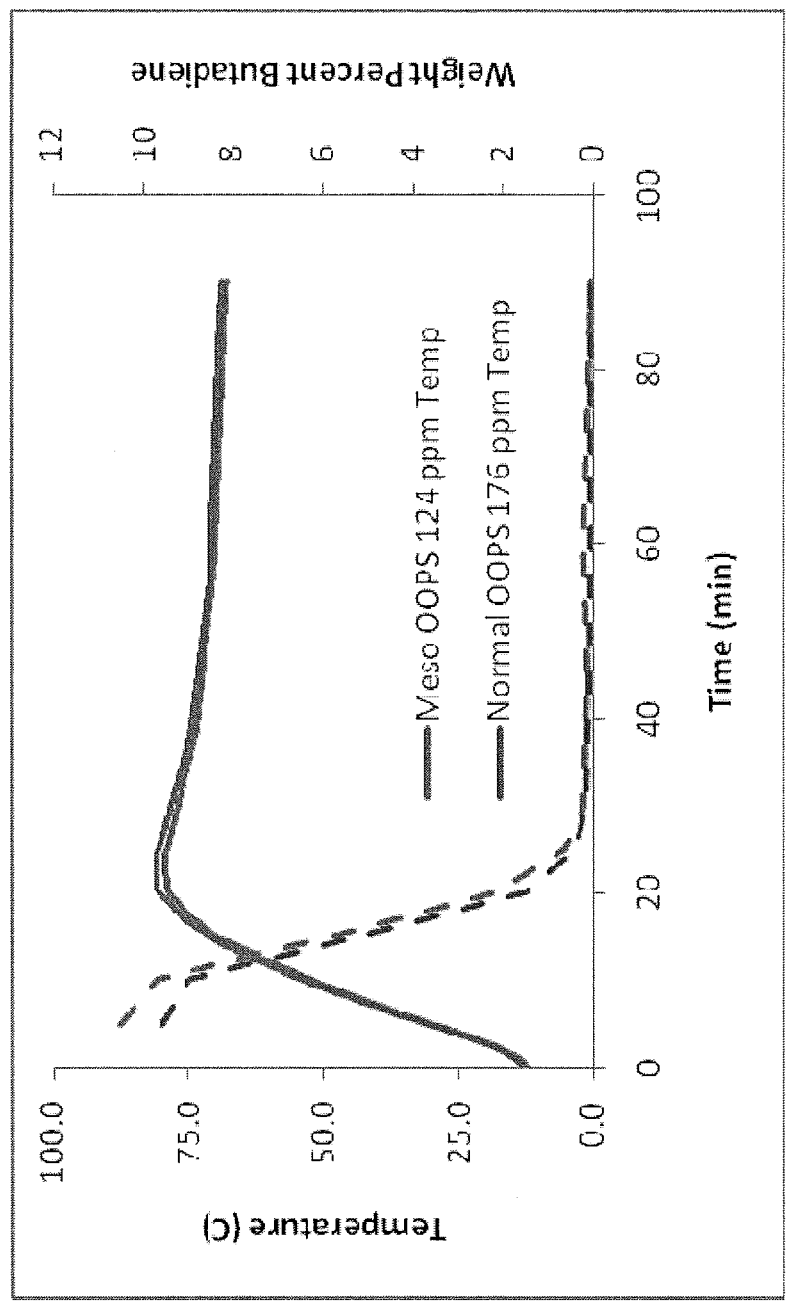
FIGURE 6: Rate of Butadiene Polymerization in the Presence of 99.8% meso 2,2-ditetrahydrofurylpropane and 49.7% meso 2,2-ditetrahydrofurylpropane.

VINYL MODIFIER COMPOSITION AND PROCESSES FOR UTILIZING SUCH COMPOSITION

CROSS-REFERENCE TO RELATED APPLICATIONS

This application is a continuation of U.S. application Ser. No. 14/682,594 which is a continuation of U.S. application Ser. No. 13/518,711 which claims priority to and benefit of PCT Application No. PCT/US2010/061795 filed Dec. 22, 2010, which claims priority to and benefit of U.S. provisional application 61/288,900 filed Dec. 22, 2009, the entire disclosure of each which is incorporated by reference herein.

FIELD OF INVENTION

The embodiments relate to an oxolanyl compound-containing composition comprising specified amounts of the meso-isomer of one or more of the oxolanyl compounds of specified structure and the use of such compositions as vinyl content modifiers in polymerization processes.

BACKGROUND

Oligomeric oxolanyl compounds have been utilized as microstructure (1,2-vinyl content) modifiers in the preparation of (co)polymers having a 1,2-microstructure of between 10 and 95 percent from a monomer system which contains at least one conjugated diene monomer. Certain of these oxolanyl compounds have at least two chiral centers that result in the existence of D, L and meso sterioisomers. Commercially available compositions of oxolanyl compounds such as 2,2-di(2-tetrahydrofuryl)propane contain a mixture of approximately 50% D, L isomers and approximately 50% of the meso isomer.

SUMMARY OF THE INVENTION

The embodiments disclosed herein relate to an oxolanyl compound-containing composition comprising specified amounts of the meso-isomer of one or more of the oxolanyl compounds of specified structure. The at least one oxolanyl compound present in the composition is selected from the group consisting of:

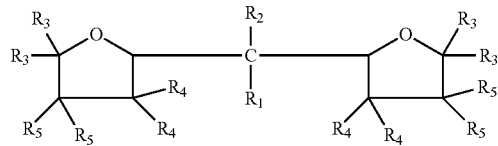

wherein $R_1$ and $R_2$ independently are hydrogen or an alkyl group and the total number of carbon atoms in —$CR_1R_2$— ranges between one and nine inclusive; $R_3$, $R_4$ and $R_5$ independently are —H or —$C_nH_{2n+1}$ wherein n=1 to 6. The composition comprises at least 52% by weight of the meso-isomer of the at least one oxolanyl compound.

Additional embodiments include a polymerization process for producing a polydiene polymer comprising polymerizing at least one conjugated diene monomer in the presence of a composition comprising at least one oxolanyl compound selected from the group consisting of:

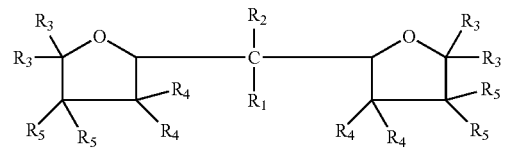

wherein $R_1$ and $R_2$ independently are hydrogen or an alkyl group and the total number of carbon atoms in —$CR_1R_2$— ranges between one and nine inclusive; $R_3$, $R_4$ and $R_5$ independently are —H or —$C_nH_{2n+1}$ wherein n=1 to 6. The composition comprises at least 52% by weight of the meso-isomer of the at least one oxolanyl compound.

Additional embodiments include a relatively high temperature polymerization process comprising polymerizing 1,3-butadiene in the presence of the oxolanyl compound 2,2-di(2-tetrahydrofuryl)propane where the oxolanyl compound comprises at least 52% by weight of the meso-isomer. Such a process produces a polydiene polymer with a vinyl content between 10 and 65%, includes the use of an organolithium anionic initiator, and is conducted at a temperature between 85° C. and 120° C.

BRIEF DESCRIPTION OF DRAWINGS

FIG. 1 shows a plot of concentration of the oxolanyl compound versus % vinyl content in the resulting polybutadiene.

FIG. 2 shows a plot of concentration of the oxolanyl compound versus vinyl content in the resulting polybutadiene.

FIG. 3 shows a $^1$H NMR of meso-2,2-ditetrahydrofurylpropane.

FIG. 4 shows a $^1$H NMR of D, L-2,2-ditetrahydrofurylpropane.

FIG. 5 shows a plot of vinyl content as a function of ppm DTHFP at various meso DTHFP concentrations.

FIG. 6 shows a plot of weight percent butadiene of the reaction mixture over time and the temperature of the reaction mixture over time.

DETAILED DESCRIPTION

The present disclosure relates to an oxolanyl compound-containing composition comprising a specified amount of the meso-isomer of one or more of the oxolanyl compounds of specified structure and the use of such compositions as vinyl content modifiers in polymerization processes. It has unexpectedly been found that the meso-isomer is more active than the commercially available and previously-utilized mixture of D, L and meso when used as a vinyl content modifier in polymerization reactions. Increased activity of the meso-isomer allows for use of relatively less of the oxolanyl compound to achieve the same result as the commercially available mixture of D, L and meso isomers. Commercially available compositions of oxolanyl compounds such as 2,2-di(2-tetrahydrofuryl)propane contain a mixture of approximately 50% (i.e., 50%+/−1%) D, L isomers and approximately 50% (i.e., 50%+/−1%) meso isomer.

Embodiments disclosed herein relate to an oxolanyl compound-containing composition comprising at least 52% by weight of the meso-isomer of one or more of the oxolanyl compounds. The at least one oxolanyl compound is selected from the group consisting of:

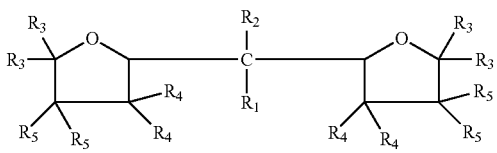

wherein $R_1$ and $R_2$ independently are hydrogen or an alkyl group and the total number of carbon atoms in —$CR_1R_2$— ranges between one and nine inclusive; $R_3$, $R_4$ and $R_5$ independently are —H or —$C_nH_{2n+1}$ wherein n=1 to 6. The composition comprises at least 52% by weight of the meso-isomer of the at least one oxolanyl compound, with the remainder being comprised of the D and L sterioisomers. In other embodiments, the composition comprises at least 55%, 60%, at least 75%, at least 90% or 100% by weight of the meso-isomer. In certain embodiments, the composition comprises only one oxolanyl compound, and in other embodiments, it comprises two, three or more different oxolanyl compounds. In certain embodiments the at least one oxolanyl compounds comprises 2,2-di(2-tetrahydrofuryl) propane.

In certain embodiments, the composition comprising at least one oxolanyl compound selected from the above-specified group may be a purified mixture resulting from the separation of a mixture of the D, L and meso forms of the oxolanyl compound by known techniques such as column chromatography or fractional distillation. It is specifically contemplated that other separation techniques, both those currently known and others developed in the future, may be utilized to achieve a composition that contains the specified amount of the meso-isomer of the at least one oxolanyl compound. In other embodiments, the meso-isomer may be preferentially produced during the synthesis of the at least one oxolanyl compound.

Additional embodiments include a polymerization process for producing a polydiene polymer comprising polymerizing at least one conjugated diene monomer in the presence of a composition comprising at least one oxolanyl compound selected from the group consisting of:

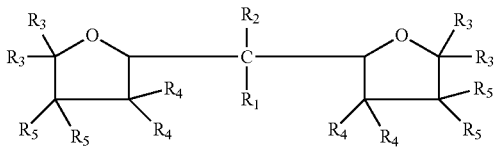

wherein $R_1$ and $R_2$ independently are hydrogen or an alkyl group and the total number of carbon atoms in —$CR_1R_2$— ranges between one and nine inclusive; $R_3$, $R_4$ and $R_5$ independently are —H or —$C_nH_{2n+1}$ wherein n=1 to 6. Various 1,3-diene monomers, as discussed below, may be utilized in the process. The composition comprises at least 52% by weight of the meso-isomer of the at least one oxolanyl compound, with the remainder being comprised of the D and L sterioisomers. In other embodiments, the composition comprises at least 55%, 60%, at least 75%, at least 90% or 100% by weight of the meso-isomer. In certain embodiments, the composition comprises only one oxolanyl compound, and in other embodiments, it comprises two, three or more different oxolanyl compounds. In certain embodiments the at least one oxolanyl compound comprises 2,2-di(2-tetrahydrofuryl) propane.

The polymerization process may optionally include the copolymerization of at least one additional monomer, including, but not limited to, at least one vinyl aromatic monomer along with the at least one conjugated diene monomer. Various vinyl aromatic monomers, as discussed below, may be utilized in the process. The resulting polydiene copolymer may take various forms including, but not limited to, random copolymers and block copolymers. In certain embodiments, the copolymer is a block copolymer of polybutadiene, polystyrene, and optionally polyisoprene. In particular embodiments, the (co)polymer is hydrogenated or partially hydrogenated.

The block copolymers can include at least one polyvinyl aromatic block and at least one polydiene block. In one embodiment, the polydiene block is characterized by a relatively high vinyl content. In one or more embodiments, the block copolymers may be defined by the formula I:

$$\alpha\text{-}V\text{-}D\text{-}\omega'$$

where V is a polyvinyl aromatic block, D is a polydiene block, $\alpha$ and $\omega'$ are each independently a hydrogen atom, a functional group, or a polymeric segment or block, and where D is characterized by a vinyl content of at least 50%.

In one or more embodiments, polyvinyl aromatic blocks include three or more mer units deriving from the polymerization of vinyl aromatic monomer. In one or more embodiments, functional groups include organic or inorganic moieties that include at least one heteroatom. In one or more embodiments, polymeric segments include homopolymers or copolymers.

In one or more embodiments, D of formula I is characterized by a vinyl content (i.e., the percentage of mer units positioned in the 1,2-microstructure) of at least 10%, in other embodiments of at least 50%, in other embodiments at least 55%, in other embodiments at least 60%, in other embodiments at least 65%, in other embodiments at least 70%, in other embodiments at least 75%, in other embodiments at least 80%, and in other embodiments at least 85%. In these or other embodiments, D of formula I is characterized by a vinyl content of less than 100%, in other embodiments less than 95%, in other embodiments less than 90%, in other embodiments less than 85%, and in other embodiments less than 80%. The vinyl content may be determined by proton NMR, and as reported herein refers to the percentage of mer units positioned in the 1,2-microstructure based on the total mer units deriving from the polymerization of conjugated diene monomer.

In one or more embodiments, the D block of formula I includes at least 250, in other embodiments at least 350, in other embodiments at least 450, and in other embodiments at least 550 mer units deriving from the polymerization of conjugated diene monomer. In these or other embodiments, the D block of formula I includes less than 800, in other embodiments less than 750, in other embodiments less than 700, in other embodiments less than 650, and in other embodiments less than 600 mer units deriving from the polymerization of conjugated diene monomer.

In one or more embodiments, the V block copolymer of formula I includes at least 50, in other embodiments at least 120, in other embodiments at least 145, in other embodiments at least 160, in other embodiments at least 180, in other embodiments at least 200, and in other embodiments at least 225 mer units deriving from the polymerization of vinyl aromatic monomer. In these or other embodiments, the V block of formula I includes less than 400, in other embodiments less than 350, in other embodiments less than 325, in other embodiments less than 300, and in other embodiments less than 280 mer units deriving from the polymerization of vinyl aromatic monomer.

In one or more embodiments, the block copolymers defined by the formula I are characterized by low levels of tapering, which may also be referred to as randomness between the blocks of the polymer chain. In other words, and for example, a vinyl aromatic block (e.g., polystyrene block) of the block copolymer will have a limited number, if any, of mer units deriving from conjugated diene (e.g., 1,3-butadiene) within the block. For purposes of this specification, tapering will refer to the level or amount of mer units (in moles) present within a given block as an impurity in that block (e.g., styrene mer units within a polybutadiene block). In one or more embodiments, the blocks of the block copolymers defined by the formula I include less than 5%, in other embodiments less than 3%, in other embodiments less than 1%, and in other embodiments less than 0.5% tapering in any given block of the block copolymer. In these or other embodiments, the blocks of the block copolymers defined by the formula I are substantially devoid of tapering, which includes that amount of tapering or less that will not have an appreciable impact on the block copolymer. In one or more embodiments, the blocks of the block copolymers defined by the formula I are devoid of tapering.

In one or more embodiments, a is a diene block deriving from the polymerization of diene monomer, and therefore the block copolymer can be defined by the formula II $$d\text{-}V\text{-}D\text{-}\omega'$$

where d is a polydiene block deriving from the polymerization of diene monomer, V, D, and $\omega'$ are as defined above with respect to formula I, and where D and d are characterized by a vinyl content of at least 50%.

In one or more embodiments, d of formula II is characterized by a vinyl content (i.e., the percentage of mer units positioned in the 1,2-microstructure) of at least 10%, in other embodiments of at least 50% in other embodiments at least 55%, in other embodiments at least 60%, in other embodiments at least 65%, in other embodiments at least 70%, in other embodiments at least 75%, in other embodiments at least 80%, and in other embodiments at least 85%. In these or other embodiments, D is characterized by a vinyl content of less than 100%, in other embodiments less than 95%, in other embodiments less than 90%, in other embodiments less than 85%, and in other embodiments less than 80%.

In one or more embodiments, d of formula II includes at least 10, in other embodiments at least 40, in other embodiments at least 60, and in other embodiments at least 80, in other embodiments at least 100, and in other embodiments at least 120 mer units deriving from the polymerization of conjugated diene monomer. In these or other embodiments, d of formula II includes less than 500, in other embodiments less than 350, in other embodiments less than 250, in other embodiments less than 200, in other embodiments less than 180, in other embodiments less than 160, and in other embodiments less than 120 mer units deriving from the polymerization of conjugated diene monomer.

In one or more embodiments, the blocks of the block copolymers defined by the formula II include less than 5%, in other embodiments less than 3%, in other embodiments less than 1%, and in other embodiments less than 0.5% tapering in any given block of the block copolymer. In these or other embodiments, the blocks of the block copolymers defined by the formula II are substantially devoid of tapering, which includes that amount of tapering or less that will not have an appreciable impact on the block copolymer. In one or more embodiments, the blocks of the block copolymers defined by the formula III are devoid of tapering.

In one or more embodiments the block copolymers may be defined by the formula III $$\alpha\text{-}V^O\text{-}D\text{-}V'\text{-}\omega'$$

where each V is independently a polyvinyl aromatic block, D is a polydiene block, $\alpha$ and $\omega'$ are each independently a hydrogen atom, a functional group, or a polymeric segment or block, and where D is characterized by a vinyl content of at least 50%.

In one or more embodiments, D of formula III is characterized by a vinyl content (i.e., the percentage of mer units positioned in the 1,2-microstructure) of at least 10%, in other embodiments of at least 50%, in other embodiments at least 55%, in other embodiments at least 60%, in other embodiments at least 65%, in other embodiments at least 70%, in other embodiments at least 75%, in other embodiments at least 80%, and in other embodiments at least 85%. In these or other embodiments, D is characterized by a vinyl content of less than 100%, in other embodiments less than 95%, in other embodiments less than 90%, in other embodiments less than 85%, and in other embodiments less than 80%.

In one or more embodiments, the D of formula III includes at least 250, in other embodiments at least 350, in other embodiments at least 450, and in other embodiments at least 550 mer units deriving from the polymerization of conjugated diene monomer. In these or other embodiments, the D block of formula III includes less than 800, in other embodiments less than 750, in other embodiments less than 700, in other embodiments less than 650, and in other embodiments less than 600 mer units deriving from the polymerization of conjugated diene monomer.

In one or more embodiments, the $V^O$ and V' blocks of formula III each independently include at least 25, in other embodiments at least 60, in other embodiments at least 75, in other embodiments at least 80, in other embodiments at least 90, in other embodiments at least 100, and in other embodiments at least 115 mer units deriving from the polymerization of vinyl aromatic monomer. In these or other embodiments, $V^O$ and V' each independently include less than 200, in other embodiments less than 175, in other embodiments less than 160, in other embodiments less than 150, and in other embodiments less than 140 mer units deriving from the polymerization of vinyl aromatic monomer.

In one or more embodiments, the ratio of $V^O$ mer units to V' mer units is at least 0.2:1, in other embodiments at least 0.4:1, in other embodiments at least 0.6:1, in other embodiments 0.8:1, in other embodiments at least 0.9:1, and in other embodiments at least 0.95:1. In these or other embodiments, the ratio of $V^O$ mer units to V' mer units is less than 4:1, in other embodiments less than 3:1, in other embodiments less than 2:1, in other embodiments less than 1.5:1, in other embodiments less than 1.1:1, and in other embodiments less than 1.05:1. In one or more embodiments, the ratio of $V^O$ mer units to V' mer units is about 1:1.

In one or more embodiments, the blocks of the block copolymers defined by the formula III include less than 5%, in other embodiments less than 3%, in other embodiments less than 1%, and in other embodiments less than 0.5% tapering in any given block of the block copolymer. In these or other embodiments, the blocks of the block copolymers defined by the formula III are substantially devoid of tapering, which includes that amount of tapering or less that will not have an appreciable impact on the block copolymer. In one or more embodiments, the blocks of the block copolymers defined by the formula III are devoid of tapering.

In one or more embodiments, a of formula III is a diene block, and therefore the block copolymer can be defined by the formula IV $$d\text{-}V^O\text{-}D\text{-}V'\text{-}\omega'$$

where d is a polydiene block, $V^O$, V', D, and ω' are as defined above with respect to Formula III, and where D and d are characterized by a vinyl content of at least 50%.

In one or more embodiments, d of formula IV is characterized by a vinyl content (i.e., the percentage of mer units positioned in the 1,2-microstructure) of at least 10%, in other embodiments of at least 50%, in other embodiments at least 55%, in other embodiments at least 60%, in other embodiments at least 65%, in other embodiments at least 70%, in other embodiments at least 75%, in other embodiments at least 80%, and in other embodiments at least 85%. In these or other embodiments, d of formula IV is characterized by a vinyl content of less than 100%, in other embodiments less than 95%, in other embodiments less than 90%, in other embodiments less than 85%, and in other embodiments less than 80%. In one or more embodiments, d of formula IV includes at least 10, in other embodiments at least 40, in other embodiments at least 60, and in other embodiments at least 80, in other embodiments at least 100, and in other embodiments at least 120 mer units deriving from the polymerization of conjugated diene monomer. In these or other embodiments, d of formula IV includes less than 500, in other embodiments less than 350, in other embodiments less than 250, in other embodiments less than 200, in other embodiments less than 180, in other embodiments less than 160, and in other embodiments less than 120 mer units deriving from the polymerization of conjugated diene monomer.

In one or more embodiments, the peak molecular weight (Mp) of the overall block copolymers may be at least 40 kg/mole, in other embodiments at least 50 kg/mole, in other embodiments at least 60 kg/mole, and in other embodiments at least 70 kg/mole. In these or other embodiments, the overall peak molecular weight of the block copolymers may be less than 150 kg/mole, in other embodiments less than 125 kg/mole, in other embodiments less than 100 kg/mole, and in other embodiments less than 90 kg/mole.

In one or more embodiments, the overall vinyl content of the block copolymers may be at least 10%, in other embodiments at least 50%, in other embodiments at least 55%, in other embodiments at least 60%, in other embodiments at least 65%, in other embodiments at least 70%, in other embodiments at least 75%, in other embodiments at least 80%, and in other embodiments at least 85%. In these or other embodiments, d of formula IV is characterized by a vinyl content of less than 100%, in other embodiments less than 95%, in other embodiments less than 90%, in other embodiments less than 85%, and in other embodiments less than 80%. As those skilled in the art will appreciate, the overall vinyl content of the block copolymers can be tailored by adjusting the vinyl content of particular diene blocks. For example, where the block copolymers are defined by the formulae II and IV, the vinyl content of the d block can be increased, without necessarily providing a corresponding increase to the D block, to affect an overall increase in the vinyl content of block copolymer.

In one or more embodiments, the blocks of the block copolymers defined by the formula IV include less than 5%, in other embodiments less than 3%, in other embodiments less than 1%, and in other embodiments less than 0.5% tapering in any given block of the block copolymer. In these or other embodiments, the blocks of the block copolymers defined by the formula IV are substantially devoid of tapering, which includes that amount of tapering or less that will not have an appreciable impact on the block copolymer. In one or more embodiments, the blocks of the block copolymers defined by the formula IV are devoid of tapering.

In one or more embodiments, the block copolymers can be synthesized by employing anionic polymerization techniques. In one or more embodiments, living polymers include anionically polymerized polymers (i.e., polymers prepared by anionic polymerization techniques). Anionically-polymerized living polymers may be formed by reacting anionic initiators with certain unsaturated monomers to propagate a polymeric structure. Throughout formation and propagation of the polymer, the polymeric structure may be anionic or "living." A new batch of monomer subsequently added to the reaction can add to the living ends of the existing chains and increase the degree of polymerization. A living polymer, therefore, includes a polymeric segment having a living or reactive end. Anionic polymerization is further described in George Odian, *Principles of Polymerization*, ch. 5 ($3^{rd}$ Ed. 1991), or Panek, 94 J. Am. Chem. Soc., 8768 (1972), which are incorporated herein by reference.

In one or more embodiments, the block copolymers can be prepared by sequential addition of the distinct monomer that give rise to the various blocks. For example, vinyl aromatic monomer can be charged and polymerized to form a living polyvinyl aromatic living polymer chain. After the vinyl aromatic monomer is consumed or substantially consumed, the conjugated diene monomer can be charged. The conjugated diene monomer adds to the living polyvinyl aromatic chain and forms a polydiene block tethered thereto. After the diene monomer is consumed or substantially consumed, additional monomer can be added to form another block tethered to the copolymer. For example, vinyl aromatic monomer can be charged to form another vinyl aromatic block. This process can be continued until the living polymer is quenched (e.g. protonated).

The process can be started by employing an anionic polymerization initiator, although as those skilled in the art appreciate, other means can be employed to initiate the polymerization.

In order to achieve the desired vinyl content of the polydiene blocks, polymerization of the diene monomer can be conducted in the presence of the oxolanyl compound-containing compositions described herein while maintaining the polymerization medium below certain threshold temperatures.

In one or more embodiments, the polymerization of the polydiene blocks (i.e., D and d) is conducted by setting the initial batch temperature (i.e., the temperature of the polymerization medium at the beginning of the polymerization of diene monomer) at temperatures below 30° C., in other embodiments below 25° C., in other embodiments below 20° C., in other embodiments below 15° C., and in other embodiments below 12° C. In these or other embodiments, the initial batch temperature may be set at above −10° C., in other embodiments above 0° C., and in other embodiments above 5° C.

In one or more embodiments, the temperature of the polymerization medium during the polymerization of conjugated diene monomer (i.e., during the formation of the polydiene blocks D or d) is maintained so as to achieve a peak polymerization temperature below 60° C., in other embodiments below 55° C., in other embodiments below 50° C., in other embodiments below 48° C., in other embodiments below 45° C., in other embodiments below 40° C., in other embodiments below 35° C., and in other embodiments below 30° C. As those skilled in the art appreciate, the initial batch temperature, as well as the peak polymerization temperature, can be controlled by employing several techniques, as well as combinations thereof. For example, the jacket temperature can be adjusted, reflux condensers can be employed, particular solvents can be selected, and the solids concentration of the polymerization can be adjusted. It has unexpectedly been discovered that the use of bis-oxolanyl propane and oligomers thereof as vinyl modifiers in the production of the block copolymers advantageously allows for peak polymerization temperatures that are relatively high and yet achieve the benefits of relatively high vinyl polydienes blocks. As those skilled in the art will appreciate, this is extremely advantageous because it allows for the production of the block copolymers at relatively high rates of polymerization yielding relatively high volume of polymer, which makes production of the block copolymers commercially viable. For example, in one or more embodiments, polymerization of the D block or blocks of the block copolymers of one or more embodiments (e.g., the polydienes blocks) can be allowed to achieve a peak polymerization temperature of at least 18° C., in other embodiments least 20° C., in other embodiments at least 23° C., in other embodiments at least 25° C., in other embodiments at least 27° C., and in other embodiments at least 30° C. In these or other embodiments, particularly where block copolymers include a diene block d (such as in formula II or IV), it has unexpectedly been discovered that advantages can be achieved by maintaining lower peak polymerization temperatures than maintained during polymerization of the D blocks. For example, in one or more embodiments, the peak polymerization temperature achieved during polymerization of the d block is at least at least 5° C., in other embodiments least 8° C., in other embodiments at least 10° C., in other embodiments at least 12° C., in other embodiments at least 15° C., and in other embodiments at least 18° C. In these or other embodiments, the peak polymerization temperature achieved during polymerization of the d block is less than 35° C., in other embodiments less than 30° C., in other embodiments less than 27° C., in other embodiments less than 25° C., and in other embodiments less than 22° C.

In one or more embodiments, it has been unexpectedly discovered that by maintaining the solids concentration of the polymerization medium during formation of the polydienes blocks defined by D (in the formulae above) at particular concentrations, benefits are realized in terms of an advantageous product produced at commercially viable rates and volumes. For example, in one or more embodiments, the solids content of the polymerization medium during formation of the D blocks is maintained at levels of at least 6%, in other embodiments at least 7%, in other embodiments at least 8%, in other embodiments at least 9%, in other embodiments at least 10%, in other embodiments at least 11%, and in other embodiments at least 12%. In these or other embodiments, the solids content of the polymerization medium during formation of the D block is maintained at levels below 22%, in other embodiments below 20%, in other embodiments below 18%, in other embodiments below 15%, and in other embodiments below 13%. Similarly, it has been unexpectedly discovered that by maintaining the solids concentration of the polymerization medium during formation of the polydienes blocks defined by d (in the formulae above) at particular concentrations, benefits are realized in terms of an advantageous product produced at commercially viable rates and volumes. For example, in one or more embodiments, the solids content of the polymerization medium during formation of the d blocks is maintained at levels of at least 0.5%, in other embodiments at least 1%, in other embodiments at least 2%, in other embodiments at least 3%, in other embodiments at least 4%, in other embodiments at least 5%, and in other embodiments at least 6%. In these or other embodiments, the solids content of the polymerization medium during formation of the d block is maintained at levels below 8%, in other embodiments below 7%, in other embodiments below 6%, in other embodiments below 5%, and in other embodiments below 4%.

The polymerization can be carried out as a batch process, a continuous process, or a semi-continuous process. In one or more embodiments, conditions may be controlled to conduct the polymerization under a pressure of from about 0.1 atmosphere to about 50 atmospheres, in other embodiments from about 0.5 atmosphere to about 20 atmosphere, and in other embodiments from about 1 atmosphere to about 10 atmospheres. In these or other embodiments, the polymerization mixture may be maintained under anaerobic conditions.

As those skilled in the art will appreciate, the solids content of the polymerization medium and the peak polymerization temperatures achieved during formation of the vinyl aromatic blocks V can be adjusted to achieve maximum efficiency without impact the vinyl content of the polydiene blocks.

In one or more embodiments, production of block copolymers occurs at technologically useful rates of production. For example, in one or more embodiments, when operating at the solids contents provided for herein for the polydienes blocks, conversion of at least 90% of the monomer to be polymerized is achieved within at least 8 hours, in other embodiments at least 6 hours, in other embodiments at least 5, in other embodiments at least 4 hours, and in other embodiments at least 3 hours. In one or more embodiments, an overall conversion of monomer is achieved at technologically useful levels; for example, conversions of at least 90%, in other embodiments at least 92%, in other embodiments at least 95%, in other embodiments at least 97%, and in other embodiments at least 99% of the monomer charged is achieved when operating at the conditions provided for herein.

In one or more embodiments, a quenching agent can be added to the polymerization mixture in order to inactivate residual living polymer chains. An antioxidant may be added along with, before, or after the addition of the quenching agent. The amount of the antioxidant employed may be in the range of, for example, 0.2% to 1% by weight of the polymer product. In one or more embodiments, a functionalizing or coupling agent may be used in lieu of or together with a quenching agent.

When the polymerization mixture has been quenched, the polymer product can be recovered from the polymerization mixture by using any conventional procedures of desolventization and drying that are known in the art. For instance, the polymer can be recovered by subjecting the polymer cement to steam desolventization, followed by drying the resulting polymer crumbs in a hot air tunnel. Alternatively, the polymer may be recovered by directly drying the polymer cement. The content of the volatile substances in the dried polymer can be below 1%, and in other embodiments below 0.5% by weight of the polymer.

The characteristics of the resultant (co)polymer can vary greatly by employing techniques that are well known in the art. The relative amounts of the at least one conjugated diene monomer and the at least one vinyl aromatic monomer present in the resulting (co)polymer can vary widely. In certain embodiments, the amount of the at least one conjugated diene monomer present in the co(polymer) ranges from 100% to 1% by weight. In other embodiments, the amount of the at least one conjugated diene monomer ranges from 100% to 10% by weight, from 100% to 15% by weight, from 100% to 20% by weight, or from 90% to 60% by weight.

The polydiene (co)polymer resulting from the polymerization process can have a varying vinyl content (1,2-vinyl content), including, but not limited to, ranging generally from 10% to less than 100%. In certain embodiments (such as relatively high temperature processes), the vinyl content of the resulting polydiene (co)polymer is 10% to 65%, at least 45%, 45% to 90%, at least 60% or 60% to 90%, or less than 100%. In other embodiments, the vinyl content of the resulting polydiene (co)polymer can be at least 50%, at least 55%, at least 70%, at least 75%, at least 80%, at least 85%, less than 95%, less than 90%, less than 85% or less than 80%.

The polydiene (co)polymer resulting from the polymerization processes described herein can have varying Mw (weight average molecular weight) and Mn (number average molecular weight). The (co)polymer will have a number average molecular weight of from 50 to 2,000 kg/mole, and preferably from 50 to 300 kg/mole as measured by using gel permeation chromatography (GPC) calibrated with polystyrene standards and adjusted for the Mark-Houwink constants for the polymer in questions. The molecular weight distribution of the (co)polymer (Mw/Mn) (also known as the polydispersity) is preferably less than 2, more preferably less than 1.5, and even more preferably less than 1.3.

In certain embodiments, the polymerization process also includes the use of at least one organometallic anionic initiator. Various organometallic anionic initiators, as discussed below, may be utilized in the process.

In certain embodiments, the meso-isomer of the oxolanyl compound is utilized in a specific molar ratio with respect to the organometallic anionic initiator. Such ratios include, but are not limited to, 0.01:10 to 0.05:5, 0.1:1, 0.1:0.7, and 1:1 (or described differently from 0.001:1 to 0.14:1, including 0.001:1, 0.01:1, 0.1:1, 0.14:1, and 1:1).

In general, the polymerization process is conducted under conditions and using reactants well known to those of ordinary skill in the art. Examples of such conditions and reactants are provided below, and should be interpreted as exemplary only and in no way limiting.

Conjugated dienes that may be utilized in the polymerization processes include, but are not limited to, 1,3-butadiene, isoprene, 1,3-pentadiene, 1,3-hexadiene, 2,3-dimethyl-1,3-butadiene, 2-ethyl-1,3-butadiene, 2-methyl-1,3 pentadiene, 3-methyl-1,3-pentadiene, 4-methyl-1,3-pentadiene, and 2,4-hexadiene. Mixtures of two or more conjugated dienes may also be utilized in co-polymerization. The preferred conjugated dienes are 1,3-butadiene, isoprene, 1,3-pentadiene, and 1,3-hexadiene.

Aromatic vinyl monomers that may be utilizes in the polymerization processes include, but are not limited to, styrene, α-methyl styrene, p-methylstyrene, and vinylnaphthalene.

Anionic polymerization initiators for use in the polymerizations processes include, but are not limited to, organosodium, organopotassium, organomagnesium, organotinlithium, and organolithium initiators. As an example of such initiators, organo-lithium compounds useful in the polymerization of 1,3-diene monomers are hydrocarbyl lithium compounds having the formula RLi, where R represents a hydrocarbyl group containing from one to 20 carbon atoms and, suitably, from 2 to 8 carbon atoms. Although the hydrocarbyl group is preferably an aliphatic group, the hydrocarbyl group can also be cycloaliphatic or aromatic. The aliphatic group can be a primary, secondary, or tertiary group, although the primary and secondary groups are most suitable. Examples of aliphatic hydrocarbyl groups include methyl, ethyl, n-propyl, isopropyl, n-butyl, sec-butyl, t-butyl, n-amyl, sec-amyl, n-hexyl, sec-hexyl, n-heptyl, n-octyl, n-nonyl, n-dodecyl, and octadecyl. The aliphatic group can contain some unsaturation, such as allyl, 2-butenyl, and the like. Cycloalkyl groups are exemplified by cyclohexyl, methylcyclohexyl, ethylcyclohexyl, cycloheptyl, cyclopentylmethyl, and methylcyclopentylethyl. Examples of aromatic hydrocarbyl groups include phenyl, tolyl, phenylethyl, benzyl, naphthyl, phenyl cyclohexyl, and the like.

Specific examples of organolithium compounds which are useful as anionic initiators in the polymerizations include, but are not limited to, n-butyl lithium, n-propyl lithium, iso-butyl lithium, tert-butyl lithium, tributyl tin lithium (described in co-owned U.S. Pat. No. 5,268,439), amyllithium, cyclohexyl lithium, and the like. Other suitable organolithium compounds for use as anionic initiators are well known to those skilled in the art. A mixture of different lithium initiator compounds also can be employed. Typical and suitable organo-lithium initiators are n-butyl lithium, tributyl tin lithium and "in situ" produced lithium hexamethyleneimide initiator prepared by reacting hexamethyleneimine and n-butyl lithium (described in co-owned U.S. Pat. No. 5,496,940).

In one or more embodiments, the functional initiator includes a lithiated thioacetal such as a lithiated dithiane. Lithiated thioacetals are known and include those described in U.S. Pat. Nos. 7,153,919, 7,319,123, 7,462,677, and 7,612,144, which are incorporated herein by reference.

In one or more embodiments, the thioacetal initiators employed can be defined by the formula

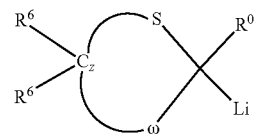

where each $R^6$ independently includes hydrogen or a monovalent organic group, $R^0$ includes a monovalent organic group, z is an integer from 1 to about 8, and ω includes sulfur, oxygen, or tertiary amino (NR, where R is an organic group).

In one or more embodiments, the functional initiators may be defined by the formula

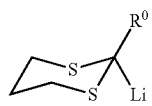

where $R^0$ includes a monovalent organic group.

Specific examples of functional initiators include 2-lithio-2-phenyl-1,3-dithiane, 2-lithio-2-(4-dimethylaminophenyl)-1,3-dithiane, 2-lithio-2-(4-dibutylaminophenyl)-1,3-dithiane, 2-lithio-[4-(4-methylpiperazino)]phenyl-1,3-dithiane, 2-lithio-[2-(4-methylpiperazino)]phenyl-1,3-dithiane, 2-lithio-[2-morpholino]phenyl-1,3-dithiane, 2-lithio-[4-morpholin-4-yl]phenyl-1,3-dithiane, 2-lithio-[2-morpholin-4-yl-pyridine-3]-1,3-dithiane, 2-lithio-[6-morpholin-4-pyridino-3]-1,3-dithiane, 2-lithio-[4-methyl-3,4-dihydro-2H-1,4-benzoxazine-7]-1,3-dithiane, and mixtures thereof.

The amount of initiator required to effect the desired polymerization can be varied over a wide range depending upon a number of factors, such as the desired polymer molecular weight and the desired physical properties for the polymer produced. In general, the amount of initiator utilized can vary from as little as 0.1 millimoles (mM) of lithium per 100 grams of monomers up to 100 mM of lithium per 100 grams of monomers, depending upon the desired polymer molecular weight.

Polymerization is usually conducted in a conventional solvent for anionic polymerizations, such as hexane, cyclohexane, benzene and the like. Various techniques for polymerization, such as batch, semi-batch and continuous polymerization can be employed.

Polymerization can be begun by charging a blend of the monomer(s) and solvent to a suitable reaction vessel, followed by the addition of the composition containing the at least one oxolanyl compound and the initiator previously described. The procedure is carried out under anhydrous, anaerobic conditions. Often, it is conducted under a dry, inert gas atmosphere. The polymerization can be carried out at any convenient temperature, such as −78° C. to 150° C. For batch polymerizations, it is suitable to maintain the peak temperature at from 50° C. to 150° C. and, also suitably, from 80° C. to 130° C. Polymerization may be allowed to continue under agitation for various amounts of time, such as 0.15 hours to 24 hours. After polymerization is complete, the product is terminated by a quenching agent, an endcapping agent and/or a coupling agent, as described herein below. The terminating agent is added to the reaction vessel, and the vessel is agitated for 0.1 hours to 4.0 hours. Quenching is usually conducted by stirring the polymer and quenching agent for 0.01 hours to 1.0 hour at temperatures of from 20° C. to 120° C. to ensure a complete reaction.

To terminate the polymerization, and thus further control polymer molecular weight, a terminating agent, coupling agent or linking agent may be employed, all of these agents being collectively referred to herein as "terminating reagents." Useful terminating, coupling or linking agents include active hydrogen compounds such as water or alcohol. Certain of these reagents may provide the resulting polymer with multifunctionality. That is, the (co)polymer may carry a functional head group from the initiator, and may also carry a second functional group as a result of the terminating reagents, coupling agents and linking agents used in the polymer synthesis. Useful functionalizing agents include those conventionally employed in the art.

Examples of useful terminating reagents include active hydrogen compounds such as water or alcohols (e.g., isopropyl alcohol and methyl alcohol); benzophenones; benzaldehydes; imidazolidones; pyrrolidinones; carbodimides; N-cyclic amides; ureas; N,N-disubstituted cyclic ureas; cyclic amides; cyclic ureas; isocyanates; Schiff-bases, including those disclosed in U.S. Pat. Nos. 3,109,871, 3,135,716, 5,332,810, 5,109,907, 5,210,145, 5,227,431, 5,329,005, 5,935,893, which are incorporated herein by reference; 4,4′bis(diethylamino) benzophenone; alkyl thiothiazolines; substituted aldimines; substituted ketimines; Michler's ketone; 1,3-dimethyl-2-imidazolidinone; 1-alkyl substituted pyrrolidinones; 1-aryl substituted pyrrolidinones; N,N-dialkylamino-benzaldehyde (such as dimethylaminobenzaldehyde or the like); 1,3-dialkyl-2-imidazolidinones (such as 1,3-dimethyl-2-imidazolidinone or the like); 1-alkyl substituted pyrrolidinones; 1-aryl substituted pyrrolidinones; tin tetrachloride; trialkyltin halides such as tributyltin chloride, as disclosed in U.S. Pat. Nos. 4,519,431, 4,540,744, 4,603,722, 5,248,722, 5,349,024, 5,502,129, and 5,877,336, which are incorporated herein by reference; cyclic amino compounds such as hexamethyleneimine alkyl chloride, as disclosed in U.S. Pat. Nos. 5,786,441, 5,916,976 and 5,552,473, which are incorporated herein by reference; cyclic sulfur-containing or oxygen containing azaheterocycles such as disclosed in U.S. Publication No. 2006/0074197 A1, U.S. Publication No. 2006/0178467 A1 and U.S. Pat. No. 6,596,798, which are incorporated herein by reference; boron-containing terminators such as disclosed in U.S. Pat. No. 7,598,322, which is incorporated herein by reference. Further, other examples include α-halo-ω-amino alkanes, such as 1-(3-bromopropyl)-2,2,5,5-tetramethyl-1-aza-2,5-disilacyclopentane, including those disclosed in copending U.S. Publication Nos. 2007/0293620 A1 and 2007/0293620 A1, which are incorporated herein by reference. Other examples include N-substituted aminoketones, N-substituted thioaminoketones, N-substituted aminoaldehydes, and N-substituted thioaminoaldehydes, including N-methyl-2-pyrrolidone or dimethylimidazolidinone (i.e., 1,3-dimethylethyleneurea) as disclosed in U.S. Pat. Nos. 4,677,165, 5,219,942, 5,902,856, 4,616,069, 4,929,679, 5,115,035, and 6,359,167, which are incorporated herein by reference; carbon dioxide; and mixtures thereof. Further examples of reactive compounds include the terminators described in co-owned U.S. Pat. Nos. 5,521,309, 5,502,131, 5,496,940, 5,066,729, and 4,616,069, the subject matter of which, pertaining to terminating agents and terminating reactions, is hereby incorporated by reference. Other useful terminating reagents can include those of the structural formula $(R)_aZX_b$, where Z is tin or silicon. Z is most suitably tin. R is an alkyl having from 1 to 20 carbon atoms; a cycloalkyl having from 3 to 20 carbon atoms; an aryl having from 6 to 20 carbon atoms, or an aralkyl having from 7 to 20 carbon atoms. For example, R can include methyl, ethyl, n-butyl, neophyl, phenyl, cyclohexyl or the like. X is a halogen, such as chlorine or bromine, or alkoxy (—OR), "a" is an integer from zero to 3, and "b" is an integer from one to 4, where a+b=4. Examples of such terminating agents include tin tetrachloride, tributyl tin chloride, butyl tin trichloride, butyl silicon trichloride, as well as tetraethylorthosilicate (TEOS), $Si(OEt)_4$, and methyl triphenoxysilane, $MeSi(OPh)_3$. Other agents include the alkoxy silanes $Si(OR)_4$, $RSi(OR)_3$, $R_2Si(OR)_2$, cyclic siloxanes (such as hexamethylcyclotrisiloxane, including those disclosed in copending U.S. Publication No. 2007/0149744 A1, which is incorporated herein by reference), and, mixtures thereof. The organic moiety R is selected from the group consisting of alkyls having from 1 to 20 carbon atoms, cycloalkyls having from 3 to 20 carbon atoms, aryls having from 6 to 20 carbon atoms and aralkyls having from 7 to 20 carbon atoms. Typical alkyls include n-butyl, s-butyl, methyl, ethyl, isopropyl and the like. The cycloalkyls include cyclohexyl, menthyl and the like. The aryl and the aralkyl groups include phenyl, benzyl and the like.

In certain embodiments, the living polymer can be treated with both coupling and functionalizing agents, which serve to couple some chains and functionalize other chains. The combination of coupling agent and functionalizing agent can be used at various molar ratios. Although the terms coupling and functionalizing agents have been employed in this specification, those skilled in the art appreciate that certain compounds may serve both functions. That is, certain compounds may both couple and provide the polymer chains with a functional group. Those skilled in the art also appreciate that the ability to couple polymer chains may depend upon the amount of coupling agent reacted with the polymer chains. For example, advantageous coupling may be achieved where the coupling agent is added in a one to one ratio between the equivalents of lithium on the initiator and equivalents of leaving groups (e.g., halogen atoms) on the coupling agent.

Exemplary coupling agents include metal halides, metalloid halides, alkoxysilanes, and alkoxystannanes.

In one or more embodiments, useful metal halides or metalloid halides may be selected from the group comprising compounds expressed by the formula (1) $R^1{}_n M^1 X_{4-n}$, the formula (2) $M^1 X_4$, and the formula (3) $M^2 X_3$, where $R^1$ is the same or different and represents a monovalent organic group with carbon number of 1 to about 20, $M^1$ in the formulas (1) and (2) represents a tin atom, silicon atom, or germanium atom, $M^2$ represents a phosphorous atom, X represents a halogen atom, and n represents an integer of 0-3.

Exemplary compounds expressed by the formula (1) include halogenated organic metal compounds, and the compounds expressed by the formulas (2) and (3) include halogenated metal compounds.

In the case where $M^1$ represents a tin atom, the compounds expressed by the formula (1) can be, for example, triphenyltin chloride, tributyltin chloride, triisopropyltin chloride, trihexyltin chloride, trioctyltin chloride, diphenyltin dichloride, dibutyltin dichloride, dihexyltin dichloride, dioctyltin dichloride, phenyltin trichloride, butyltin trichloride, octyltin trichloride and the like. Furthermore, tin tetrachloride, tin tetrabromide and the like can be exemplified as the compounds expressed by formula (2).

In the case where $M^1$ represents a silicon atom, the compounds expressed by the formula (1) can be, for example, triphenylchlorosilane, trihexylchlorosilane, trioctylchlorosilane, tributylchlorosilane, trimethylchlorosilane, diphenyldichlorosilane, dihexyldichlorosilane, dioctyldichlorosilane, dibutyldichlorosilane, dimethyldichlorosilane, methyltrichlorosilane, phenyltrichlorosilane, hexyltrichlorosilane, octyltrichlorosilane, butyltrichlorosilane, methyltrichlorosilane and the like. Furthermore, silicon tetrachloride, silicon tetrabromide and the like can be exemplified as the compounds expressed by the formula (2). In the case where $M^1$ represents a germanium atom, the compounds expressed by the formula (1) can be, for example, triphenylgermanium chloride, dibutylgermanium dichloride, diphenylgermanium dichloride, butylgermanium trichloride and the like. Furthermore, germanium tetrachloride, germanium tetrabromide and the like can be exemplified as the compounds expressed by the formula (2). Phosphorous trichloride, phosphorous tribromide and the like can be exemplified as the compounds expressed by the formula (3). In one or more embodiments, mixtures of metal halides and/or metalloid halides can be used.

In one or more embodiments, useful alkoxysilanes or alkoxystannanes may be selected from the group comprising compounds expressed by the formula (1) $R^1{}_n M^1 (OR)_{4-n}$, where $R^1$ is the same or different and represents a monovalent organic group with carbon number of 1 to about 20, $M^1$ represents a tin atom, silicon atom, or germanium atom, OR represents an alkoxy group where R represents a monovalent organic group, and n represents an integer of 0-3.

Exemplary compounds expressed by the formula (4) include tetraethyl orthosilicate, tetramethyl orthosilicate, tetrapropyl orthosilicate, tetraethoxy tin, tetramethoxy tin, and tetrapropoxy tin.

The amount of terminating agent required to effect the desired termination of the polymerization can be varied over a wide range depending upon a number of factors, such as the desired polymer molecular weight and the desired physical properties for the polymer produced. In general, the amount of terminating agent utilized can vary from a molar ratio of 0.1:5 to 0.5:1.5 to 0.8:1.2 (terminating agent:Li).

The practice of polymerization processes described herein is not limited solely to the terminating reagents described herein, since other compounds that are reactive with the polymer bound carbon-lithium moiety can be selected to provide a desired functional group. In other words, the foregoing listing of terminating reagents is not to be construed as limiting but rather as enabling. While a terminating reagent can be employed, practice of the present embodiments are not limited to a specific reagent or class of such compounds.

While terminating to provide a functional group on the terminal end of the polymer is desirable, it is further desirable to terminate by a coupling reaction with, for example, tin tetrachloride or other coupling agent such as silicon tetrachloride or esters. High levels of tin coupling are desirable in order to maintain good processability in the subsequent manufacturing of rubber products. It is preferred that the polymers for use in the vulcanizable elastomeric compositions according to the present embodiments have at least 25 percent tin coupling. That is, 25 percent of the polymer mass after coupling is of higher molecular weight than the polymer before coupling as measured, for example, by gel permeation chromatography. Suitably, before coupling, the polydispersity (the ratio of the weight average molecular weight to the number average molecular weight) of polymers, which can be controlled over a wide range, is preferably less than 2, more preferably less than 1.5, and even more preferably less than 1.3.

As noted above, various techniques known in the art for carrying out the polymerization processes described herein can be used to produce polydiene (co)polymers, without departing from the scope of the present embodiments.

In additional embodiments the polymerization process comprising polymerizing 1,3-butadiene in the presence of the oxolanyl compound 2,2-di(2-tetrahydrofuryl)propane where the oxolanyl compound comprises at least 52% by weight of the meso-isomer. Such a process produces a polydiene polymer with a vinyl content between 20 and 65%, includes the use of an organolithium anionic initiator, and is conducted at a temperature between 85° C. and 120° C.

The (co)polymers prepared utilizing the compositions and processes disclosed herein are particularly useful for use in preparing tire components (e.g., treads and sidewalls). Such tire components can be prepared by using such (co)polymers alone or together with other rubbery polymers or elastomers. Preferably, the (co)polymers are employed in tread formulations, and these tread formulations will include from 10 to 100% by weight of the (co)polymer based on the total rubber within the formulation (i.e., 10 to 100 parts of the (co) polymer(s) per 100 parts of total rubber or phr). More preferably, the tread formulation will include from 35 to 80% by weight, and more preferably from 50 to 80% by weight of the (co)polymer based on the total weight of the rubber within the formulation.

In preparing the vulcanizable compositions of matter (or rubber compositions) containing the co(polymers) prepared utilizing the compositions and processes disclosed herein, and optionally, one or more other rubber polymers, at least one filler may be combined and mixed or compounded with a rubber component, which includes the (co)polymers disclosed herein as well as other optional rubber polymers. Other rubbery elastomers or polymers that may be used include natural and synthetic elastomers. The synthetic elastomers typically derive from the polymerization of conjugated diene monomers. These conjugated diene monomers may be copolymerized with other monomers such as vinyl aromatic monomers. Other rubbery elastomers may derive from the polymerization of ethylene together with one or more $\alpha$-olefins and optionally one or more diene monomers.

Useful rubbery elastomers include, but are not limited to, natural rubber, synthetic polyisoprene, polybutadiene, polyisobutylene-co-isoprene, neoprene, poly(ethylene-co-propylene), poly(styrene-co-butadiene), poly(styrene-co-isoprene), and poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched and star shaped. Other ingredients that are typically employed in rubber compounding may also be added.

The rubber compositions may include fillers such as inorganic and organic fillers. Commonly utilized organic fillers include carbon black and starch. Commonly utilized inorganic fillers include silica, aluminum hydroxide, magnesium hydroxide, clays (hydrated aluminum silicates), and mixtures thereof.

In one or more embodiments, silica (silicon dioxide) includes wet-process, hydrated silica produced by a chemical reaction in water, and precipitated as ultra-fine spherical particles. In one embodiment, the silica has a surface area of about 32 to about 400 $m^2/g$, in another embodiment about 100 to about 250 $m^2/g$, and in yet another embodiment, about 150 to about 220 $m^2/g$. The pH of the silica filler in one embodiment is about 5.5 to about 7 and in another embodiment about 5.5 to about 6.8. Commercially available silicas include Hi-Sil™ 215, Hi-Sil™ 233, Hi-Sil™ 255LD, and Hi-Sil™ 190 (PPG Industries; Pittsburgh, Pa.), Zeosil™ 1165MP and 175GRPlus (Rhodia), Vulkasil™ (Bary AG), Ultrasil™ VN2, VN3 (Degussa), and HuberSil™ 8745 (Huber).

In one or more embodiments, the carbon blacks may include any of the commonly available, commercially-produced carbon blacks. These include those having a surface area (EMSA) of at least 20 $m^2/gram$ and in other embodiments at least 35 $m^2/gram$ up to 200 $m^2/gram$ or higher. Surface area values include those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks that may be utilized include acetylene blacks. Mixtures of two or more of the above blacks can be used. Exemplary carbon blacks include those bearing ASTM designation (D-1765-82a) N-110, N-220, N-339, N-330, N-351, N-550, and N-660. In one or more embodiments, the carbon black may include oxidized carbon black.

In one embodiment, silica may be used in an amount of from about 5 to about 100 parts by weight parts per hundred rubber (phr), in another embodiment from about 10 to about 90 parts by weight phr, in yet another embodiment from about 15 to about 80 parts by weight phr, and in still another embodiment from about 25 to about 75 parts by weight phr.

As is well-known to those of skill in the art, a multitude of rubber curing agents may be employed. For example, sulfur or peroxide-based curing systems may be employed. Also, see Kirk-Othmer, ENCYCLOPEDIA OF CHEMICAL TECHNOLOGY, $3^{rd}$ Edition, Wiley Interscience, New York 1982, Vol. 20, pp. 365-468, particularly VULCANIZATION AGENTS AND AUXILIARY MATERIALS pp. 390-402, or Vulcanization by A. Y. Coran, ENCYCLOPEDIA OF POLYMER SCIENCE AND ENGINEERING, $2^{nd}$ Edition, John Wiley & Sons, Inc., 1989, which are incorporated herein by reference. Vulcanizing agents may be used alone or in combination. In one or more embodiments, the preparation of vulcanizable compositions and the construction and curing of the tire is not affected.

Other ingredients that may be employed are also well known to those of skill in the art and include accelerators, oils, waxes, scorch inhibiting agents, processing aids, zinc oxide, tackifying resins, reinforcing resins, fatty acids such as stearic acid, peptizers, and one or more additional rubbers. Examples of oils include paraffinic oils, aromatic oils, naphthenic oils, vegetable oils other than castor oils, and low PCA oils including MES, TDAE, SRAE, heavy naphthenic oils, and black oils.

In one or more embodiments, the vulcanizable rubber composition may be prepared by forming an initial masterbatch that includes the rubber component and filler (the rubber component optionally including other polymers and rubbery polymers such as functional polymers). This initial masterbatch may be mixed at a starting temperature of from about 25° C. to about 125° C. with a discharge temperature of about 135° C. to about 180° C. To prevent premature vulcanization (also known as scorch), this initial masterbatch may exclude vulcanizing agents. Once the initial masterbatch is processed, the vulcanizing agents may be introduced and blended into the initial masterbatch at low temperatures in a final mix stage, which preferably does not initiate the vulcanization process. Optionally, additional mixing stages, sometimes called remills, can be employed between the masterbatch mix stage and the final mix stage. Various ingredients including polymers and copolymers can be added during these remills. Rubber compounding techniques and the additives employed therein are generally known as disclosed in The Compounding and Vulcanization of Rubber, in Rubber Technology (2nd Ed. 1973).

The mixing conditions and procedures applicable to silica-filled tire formulations are also well known as described in U.S. Pat. Nos. 5,227,425, 5,719,207, 5,717,022, and European Patent No. 890,606, all of which are incorporated herein by reference. In one or more embodiments, where silica is employed as a filler (alone or in combination with other fillers), a coupling and/or shielding agent may be added to the rubber formulation during mixing. Useful coupling and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference. In one embodiment, the initial masterbatch is prepared by including the rubbery polymers and/or copolymers and silica in the substantial absence of coupling and shielding agents. It is believed that this procedure will enhance the opportunity that a functional polymer will react or interact with silica before competing with coupling or shielding agents, which can be added later curing remills.

Where the vulcanizable rubber compositions are employed in the manufacture of tires, these compositions can be processed into tire components according to ordinary tire manufacturing techniques including standard rubber shaping, molding and curing techniques. Any of the various rubber tire components can be fabricated including, but not limited to, treads, sidewalls, belt skims, and carcass. Typically, vulcanization is effected by heating the vulcanizable composition in a mold; e.g., it may be heated to about 140° C. to about 180° C. Cured or crosslinked rubber compositions may be referred to as vulcanizates, which generally contain three-dimensional polymeric networks that are thermoset. The other ingredients, such as processing aides and fillers, may be evenly dispersed throughout the vulcanized network. Pneumatic tires can be made as discussed in U.S. Pat. Nos. 5,866,171, 5,876,527, 5,931,211, and 5,971,046, which are incorporated herein by reference.

This application discloses several numerical range limitations that support any range within the disclosed numerical ranges even though a precise range limitation is not stated verbatim in the specification because the embodiments could be practiced throughout the disclosed numerical ranges. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the claims.

Examples

Isolation of the Diastereoisomers of 2,2-Di(2-Tetrahydrofuryl)Propane

A commercially obtained quantity of 2,2-di(2-tetrahydrofuryl)propane (Penn Specialty Chemicals) was purified using column chromatography to isolate the diastereoisomers. The column was prepared with a stationary phase of 230-400 mesh size silica gel (available from Fisher Scientific) and a mobile phase of 20% diethyl ether and 80% n-pentane. Repeated 25 mL aliquots of the mobile phase were utilized. Pure meso-2,2-di(2-tetrahydrofuryl)propane was isolated as a first fraction. The yield of the meso-isomer was approximately 20% of the original amount of 2,2-di(2-tetrahydrofuryl)propane. Pure D,L-2,2-di(2-tetrahydrofuryl)propane was isolated as the second fraction and the yield was also approximately 20% of the original amount of 2,2-di(2-tetrahydrofuryl)propane. GC-FID analysis (of the starting 2,2-di(2-tetrahydrofuryl)propane and the two diastereoisomers confirmed the purity of the first two fractions. Conditions included: Use of Supelco Equity 1 column (30 m×0.32 mm×5.0 µm); GC-Injection port temperature: 260° C.; Injection Port split ratio: 20:1; carrier gas ran in the constant flow mode with 1.5 mL/minute; FID temperature: 280° C.; sample size: 1 µl. Column Oven Program:

| Rate ° C./min | Temperature/° C. | Time/min | Total/min |
|---|---|---|---|
| Initial | 55 | 1.0 | 1.0 |
| 10 | 280 | 12.5 | 36.0 |

Structures were also confirmed by $^1$H-NMR (as illustrated in FIGS. 3 and 4). In FIG. 3, note the two peaks for methyls indicating the meso form. In FIG. 4, note the one peak for the methyls indicating D, L form.

Polymerization of 1,3-Butadiene

To an 800 mL nitrogen-purged bottle fitted with a crimp seal cap was added 183.5 g of 21.8 weight percent 1,3-butadiene in hexanes, 0.24 mL 1.65 M n-butyllithium in hexanes, and a varying amount (Table 1, below) of meso, DL or a commercially available 2,2-di(2-tetrahydrofuryl)propane (containing 51% by weight of the meso isomer and approximately 49% by weight of the D and L isomers and indicated below as "mixed"). The bottle was then placed in a 50° C. bath for 4 hours. Concentration of the 2,2-di(2-tetrahydrofuryl)propane ("DTHFP") was measured by GC, vinyl content by $^1$H-NMR, and molecular weight by GPC using the appropriate Mark Houwink constant (polystyrene standard).

Properties of the resulting polymers are listed in Table 1 and a plot of concentration of the oxolanyl compound versus % vinyl content in the resulting polybutadiene is shown in FIG. 1. The meso form of the oxolanyl compound was more effective in producing vinyl content that either the mixture of the DL form. In other words, a relatively lesser amount of the meso form was needed to produce the same vinyl content.

TABLE 1

| Type | Concentration (ppm) | % Vinyl in Resulting Polymer | Mn (kg/mol) of Resulting Polymer |
|---|---|---|---|
| Mixed | 26 | 30.2 | 93.0 |
| Mixed | 66 | 47.1 | 88.5 |
| Mixed | 73 | 46.4 | 106.0 |
| Mixed | 81 | 50.7 | 94.4 |
| Mixed | 134 | 60.1 | 94.2 |
| Mixed | 147 | 58.2 | 100.6 |
| Mixed | 350 | 71.4 | 96.3 |
| Meso | 44 | 46.4 | 91.4 |
| Meso | 66 | 54.1 | 90.0 |
| Meso | 109 | 58.8 | 102.8 |
| Meso | 224 | 67.1 | 105.6 |
| D, L | 42 | 29 | 89.8 |
| D, L | 44 | 31.6 | 107.3 |
| D, L | 83 | 42.1 | 94.4 |
| D, L | 89 | 44.6 | 94.4 |
| D, L | 108 | 50.5 | 93.4 |

Polymerization of 1,3-Butadiene and Styrene

To an 800 mL nitrogen-purged bottle fitted with a crimp seal cap was added 23.5 g of 34 weight percent styrene in hexanes and 14.35 g of 22.3 weight percent 1,3-butadiene in hexanes, 0.24 mL 1.65 M n-butyllithium in hexanes, and a varying amount (Table 2, below) of meso (100% meso), pure DL (100% DL) or a commercially available 2,2-di(2-tetrahydrofuryl)propane (containing approximately 50% by weight of the meso isomer and approximately 50% by weight of the D and L isomers and indicated below as "mixed"). The bottle was then placed in a 50° C. bath for 4 hours. Concentration of the 2,2-di(2-tetrahydrofuryl)propane was measured by GC, vinyl content by $^1$H-NMR, and molecular weight by GPC using the appropriate Mark Houwink constant (polystyrene standard).

Properties of the resulting polymers are listed in Table 2 and a plot of concentration of the oxolanyl compound versus % vinyl content in the resulting polybutadiene is shown in FIG. 2. Again, the meso form of the oxolanyl compound was more effective in producing vinyl content that either the mixture of the DL form. In other words, a relatively lesser amount of the meso form was needed to produce the same vinyl content.

TABLE 2

| Type | Concentration (ppm) | % Vinyl in Resulting Polymer | Mn (kg/mol) of Resulting Polymer |
|---|---|---|---|
| Mixed | 71 | 45.6 | 104.9 |
| Mixed | 71 | 47.6 | 99.5 |
| Mixed | 145 | 55.2 | 99.2 |
| Meso | 107 | 57.1 | 97.5 |
| D, L | 42 | 30.9 | 100 |
| D, L | 79 | 42.0 | 104.4 |

Influence of Meso/D,L DTHFP on Vinyl in Polybutadiene Polymerization

To an 800 mL nitrogen purged bottle was added 214 g hexanes and 186 g of 21.5 wt % butadiene in hexanes. Then, either 0.08 mL, 0.15 mL, 0.30 mL, 0.60 mL, or 1.0 mL of approximately 0.4 M 2,2-ditetrahydrofurylpropane of varying meso concentrations (99.8%, 88.1%, 87.3%, 75%, 65.3%, 54.9%, 44.9%, and 5.8%) was added. Afterwards, 0.24 mL of 1.65 M n-butyllithium in hexanes was added and the bottles were heated to 50° C. for four hours. $^1$H NMR was used to determine vinyl content in the polybutadiene samples and GC was used to determine the concentration of 2,2-ditetrahydrofurylpropane.

Properties of the resulting polymers are listed in Table 3 and a plot of vinyl content as a function of ppm DTHFP at various Meso DTHFP concentrations is shown in FIG. 5.

TABLE 3

| % Meso DTHFP | ppm DTHFP | % Vinyl |
|---|---|---|
| 99.8 | 14.00 | 17.3 |
| 99.8 | 17.14 | 21.7 |
| 99.8 | 40.13 | 42.5 |
| 99.8 | 83.58 | 58.1 |
| 99.8 | 135.74 | 67.8 |
| 88.1 | 11.60 | 17.9 |
| 88.1 | 23.39 | 28.5 |
| 88.1 | 49.98 | 42.8 |
| 88.1 | 96.04 | 58.5 |
| 88.1 | 176.70 | 67.8 |
| 87.3 | 23.15 | 24 |
| 87.3 | 28.53 | 29.2 |
| 87.3 | 56.89 | 42.7 |
| 87.3 | 103.13 | 57.5 |
| 87.3 | 172.60 | 66.2 |
| 75 | 11.42 | 20.1 |
| 75 | 44.29 | 36.3 |
| 75 | 53.58 | 42.2 |
| 75 | 109.94 | 57.4 |
| 75 | 176.01 | 68 |
| 65.3 | 7.52 | 13.9 |
| 65.3 | 22.55 | 25.6 |
| 65.3 | 49.98 | 39.2 |
| 65.3 | 90.14 | 54.7 |
| 65.3 | 147.60 | 63.7 |
| 54.9 | 11.94 | 17 |
| 54.9 | 17.85 | 21.6 |
| 54.9 | 39.86 | 34.2 |
| 54.9 | 88.82 | 49.2 |
| 54.9 | 154.06 | 59.9 |
| 44.9 | 13.75 | 16.8 |
| 44.9 | 24.55 | 23.5 |
| 44.9 | 47.26 | 35.8 |
| 44.9 | 103.45 | 50.7 |
| 44.9 | 155.57 | 61.3 |
| 5.8 | 12.34 | 17.1 |
| 5.8 | 28.73 | 22.1 |
| 5.8 | 54.30 | 31.6 |
| 5.8 | 98.51 | 44.3 |
| 5.8 | 170.81 | 53.9 |

Kinetics of Polybutadiene Polymerization

The rate of anionic butadiene polymerization was next examined for polymerization modified in the presence of 99.8% meso 2,2-ditetrahydrofurylpropane and 49.7% meso 2,2-ditetrahydrofurylpropane.

Butadiene Polymerization Rate Utilizing 99.8% Meso-2,2-Ditetrahydrofurylpropane

To a 7.57 L nitrogen purged, stainless steel reactor was added 0.54 kg of anhydrous hexanes and 1.63 kg of 20.9 weight percent 1,3-butadiene in hexanes. Then, 5.73 mL of 0.36 M 2,2-ditetrahydrofurylpropane (99.8% meso) in hexanes and 1.37 mL 1.65 M butyl lithium in hexanes was added at 11.7° C. (The 99.8% meso 2,2-ditetrahydrofurylpropane was isolated using the column chromatography procedure described above.) The reactor jacket was set at 71.1° C. Samples were taken at 5, 10, 15, 20, 25, 30, 45, 60, and 90 minutes and measured for conversion and molecular weight. Samples at 20, 30 and 60 minutes were examined for vinyl content by $^1$H NMR. GC was used to measure the concentration of 1,3-butadiene and 2,2-ditetrahydrofurylpropane (124 ppm) in the reaction.

Properties of the resulting polymers, from samples taken at the indicated reaction times, are listed in Table 4 and a plot showing the weight percent butadiene of the reaction mixture over time and the temperature of the reaction mixture over time is shown in FIG. 6. The dashed lines of FIG. 6 plot the weight percent butadiene of the reaction mixture over time and the solid lines of FIG. 6 plot the temperature of the reaction mixture over time.

TABLE 4

| Reaction Time (minutes) | Weight Percent Butadiene | Molecular Weight (kg/mol) | % Vinyl |
|---|---|---|---|
| 5 | 10.51 | 8.2 | |
| 10 | 9.72 | 27.5 | |
| 15 | 5.85 | 56.9 | |
| 20 | 2.13 | 92 | 55.2 |
| 25 | 0.6 | 103.2 | |
| 30 | 0.21 | 106.9 | 52.1 |
| 45 | 0.12 | 111.4 | |
| 60 | 0.18 | 114.2 | 51.7 |
| 90 | 0.03 | 117.9 | |

Butadiene Polymerization Rate Utilizing 49.7% Meso-2,2-Ditetrahydrofurylpropane

To a 7.57 L nitrogen purged, stainless steel reactor was added 0.54 kg of anhydrous hexanes and 1.63 kg of 20.9 weight percent 1,3-butadiene in hexanes. Then, 0.82 ml, of 1.6 M 2,2-ditetrahydrofurylpropane (49.7% meso) in hexanes and 1.37 mL 1.65 M butyl lithium in hexanes were added at 12.1° C. (The 49.7% meso 2,2-ditetrahydrofurylpropane was used as received from the supplier.) The reactor jacket was set at 71.1° C. Samples were taken at 5, 10, 15, 20, 25, 30, 45, 60, and 90 minutes and measured for conversion and molecular weight. Samples taken at 20, 30 and 60 minutes were examined for vinyl content by $^1$H NMR. GC was used to measure the concentration of 1,3-butadiene and 2,2-ditetrahydrofurylpropane (176 ppm) in the reaction.

Properties of the resulting polymers are listed in Table 5 and a plot showing the weight percent butadiene of the reaction mixture over time and the temperature of the reaction mixture over time is shown in FIG. 6. The dashed lines of FIG. 6 plot the weight percent butadiene of the reaction mixture over time and the solid lines of FIG. 6 plot the temperature of the reaction mixture over time.

TABLE 5

| Reaction Time (minutes) | Weight Percent Butadiene | Molecular Weight (kg/mol) | % Vinyl |
|---|---|---|---|
| 5 | 9.59 | | |
| 10 | 9 | 31.9 | |
| 15 | 5.23 | 64.6 | |
| 20 | 1.5 | 95.8 | 52.6 |
| 25 | 0.4 | 106.9 | |
| 30 | 0.17 | 110 | 50 |
| 45 | 0.1 | 112.1 | |
| 60 | 0.06 | 114.6 | 49.8 |
| 90 | 0.03 | 118.6 | |

The experimental examples show that as the meso content increases at constant DTHFP concentration, the vinyl content of the resulting polymer increases. The last two experimental examples show that with reactor runs using approximately 60% of 99.8% meso DTHFP (124 ppm) gives similar vinyl to using 100% of a ~50% meso DTHFP (176 ppm).

We claim:

1. A vinyl content modifier composition comprising at least one oxolanyl compound selected from the group consisting of:

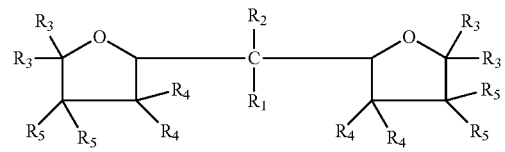

wherein $R^1$ and $R^2$ independently are hydrogen or an alkyl group and the total number of carbon atoms in —$CR^1R^2$—ranges between one and nine inclusive; $R^3$, $R^4$ and $R^5$ independently are —H or —$C_nH_{2n+1}$ wherein n=1 to 6, and wherein at least 60% by weight of the least one oxolanyl compound comprises meso-isomer.

2. The vinyl content modifier composition of claim 1, wherein at least 65% by weight of the at least one oxolanyl compound comprises meso-isomer.

3. The vinyl content modifier composition of claim 1, wherein at least 75% by weight of the at least one oxolanyl compound comprises meso-isomer.

4. The vinyl content modifier composition of claim 1, wherein at least 99% by weight of the at least one oxolanyl compound comprises meso-isomer.

5. The vinyl content modifier composition of claim 1 wherein 65-99% by weight of the at least one oxolanyl compound comprises meso-isomer.

6. The vinyl content modifier composition of claim 1, wherein the at least one oxolanyl compound comprises 2,2-di(2-tetrahydrofuryl)propane.

7. The vinyl content modifier composition of claim 6, wherein at least 75% by weight of the at least one oxolanyl compound comprises meso-isomer.

8. The vinyl content modifier composition of claim 6, wherein 65-99% by weight of the at least one oxolanyl compound comprises meso-isomer.

9. A vinyl content modifier composition consisting of at least one oxolanyl compound selected from the group consisting of:

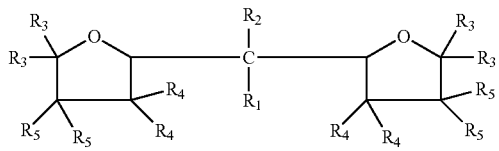
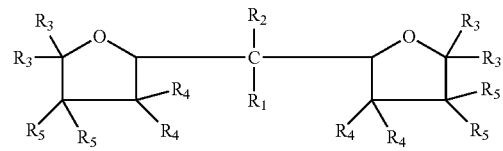

wherein $R^1$ and $R^2$ independently are hydrogen or an alkyl group and the total number of carbon atoms in —$CR^1R^2$- ranges between one and nine inclusive; $R^3$, $R^4$ and $R^5$ independently are —H or —$C_nH_{2n+1}$ wherein n=1 to 6, and wherein at least 60% by weight of the least one oxolanyl compound comprises meso-isomer.

10. The vinyl content modifier composition of claim 9, wherein at least 65% by weight of the at least one oxolanyl compound comprises meso-isomer.

11. The vinyl content modifier composition of claim 9, wherein at least 75% by weight of the at least one oxolanyl compound comprises meso-isomer.

12. The vinyl content modifier composition of claim 9, wherein at least 99% by weight of the at least one oxolanyl compound comprises meso-isomer.

13. The vinyl content modifier composition of claim 9, wherein 65-99% by weight of the at least one oxolanyl compound comprises meso-isomer.

14. The vinyl content modifier composition of claim 9, wherein the at least one oxolanyl compound comprises 2,2-di(2-tetrahydrofuryl)propane.

15. The vinyl content modifier composition of claim 14, wherein at least 75% by weight of the at least one oxolanyl compound comprises meso-isomer.

16. The vinyl content modifier composition of claim 14, wherein 65-99% by weight of the at least one oxolanyl compound comprises meso-isomer.

17. A vinyl content modifier composition comprising at least one oxolanyl compound selected from the group consisting of:

wherein $R^1$ and $R^2$ independently are hydrogen or an alkyl group and the total number of carbon atoms in —$CR^1R^2$- ranges between one and nine inclusive; $R^3$, $R^4$ and $R^5$ independently are —H or —$C_nH_{2n+1}$ wherein n=1 to 6, wherein at least 60% by weight of the least one oxolanyl compound comprises meso-isomer, and wherein the composition has a molarity of at least 0.36 M.

18. The vinyl content modifier composition of claim 17, wherein the molarity is at least 1.6 M.

19. The vinyl content modifier composition of claim 17, wherein at least 65% by weight of the at least one oxolanyl compound comprises meso-isomer.

20. The vinyl content modifier composition of claim 17, wherein at least 75% by weight of the at least one oxolanyl compound comprises meso-isomer.

21. The vinyl content modifier composition of claim 17, wherein 65-99% by weight of the at least one oxolanyl compound comprises meso-isomer.

22. The vinyl content modifier composition of claim 17, wherein the at least one oxolanyl compound comprises 2,2-di(2-tetrahydrofuryl)propane.

23. The vinyl content modifier composition of claim 18, wherein the at least one oxolanyl compound comprises 2,2-di(2-tetrahydrofuryl)propane.

24. The vinyl content modifier composition of claim 19, wherein the at least one oxolanyl compound comprises 2,2-di(2-tetrahydrofuryl)propane.

25. The vinyl content modifier composition of claim 20, wherein the at least one oxolanyl compound comprises 2,2-di(2-tetrahydrofuryl)propane.

26. The vinyl content modifier composition of claim 21, wherein the at least one oxolanyl compound comprises 2,2-di(2-tetrahydrofuryl)propane.

* * * * *